United States Patent
Wiebe et al.

(10) Patent No.: US 10,105,098 B2
(45) Date of Patent: *Oct. 23, 2018

(54) GARMENT INTEGRATED SENSING SYSTEM AND METHOD

(71) Applicant: MAD Apparel, Inc., Redwood City, CA (US)

(72) Inventors: Christopher John Wiebe, Redwood City, CA (US); Hamid Hameed Butt, Redwood City, CA (US)

(73) Assignee: MAD Apparel, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/884,218

(22) Filed: Jan. 30, 2018

(65) Prior Publication Data

US 2018/0153471 A1 Jun. 7, 2018

Related U.S. Application Data

(63) Continuation of application No. 14/937,767, filed on Nov. 10, 2015, now Pat. No. 9,913,611.

(60) Provisional application No. 62/077,781, filed on Nov. 10, 2014.

(51) Int. Cl.
*G08C 19/22* (2006.01)
*A61B 5/00* (2006.01)

(52) U.S. Cl.
CPC .......... *A61B 5/6804* (2013.01); *A61B 5/0015* (2013.01); *A61B 2562/06* (2013.01); *A61B 2562/08* (2013.01)

(58) Field of Classification Search
CPC ............ A61B 2562/06; A61B 2562/08; A61B 5/0015; A61B 5/6804
See application file for complete search history.

(56) References Cited

U.S. PATENT DOCUMENTS

2014/0278125 A1* 9/2014 Balakrishnan ...... G06F 19/3481
702/19

* cited by examiner

*Primary Examiner* — Brian Zimmerman
*Assistant Examiner* — Kevin Lau
(74) *Attorney, Agent, or Firm* — Fenwick & West LLP

(57) ABSTRACT

A system for monitoring biometric signals of a user comprising: a set of wireless sensor interfaces coupled to a garment, each of the wireless sensor interfaces comprising: 1) an electrode layer comprising a receiving region, 2) a positional identifier, associated with a position on the garment, and 3) a retention subsystem; a set of wireless sensor modules, each of the set of wireless sensor modules comprising: a contact region electrically coupleable to the receiving region of the electrode layer, a set of sensors configured to detect a set of biometric signal types, and a positional interrogator configured to identify the position associated with the corresponding wireless sensor interface; and a control module, communicatively coupled to the set of wireless sensor modules, wherein the control module queries a subset of the set of biometric signal types for transmission from each of the set of wireless sensor modules based on their positions.

20 Claims, 9 Drawing Sheets

GARMENT INTEGRATED SENSING SYSTEM AND METHOD

CROSS-REFERENCE TO RELATED APPLICATIONS

This application is a continuation of U.S. application Ser. No. 14/937,767, filed Nov. 10, 2015, which claims the benefit of U.S. Provisional Application No. 62/077,781, filed Nov. 10, 2014, each of which are incorporated by reference in their entirety.

TECHNICAL FIELD

This invention relates generally to the biometric device field, and more specifically to a new and useful garment integrated sensing system and method.

BACKGROUND

Tracking biometric parameters resulting from periods of physical activity can provide profound insights into improving one's performance and overall health. Historically, users have tracked their exercise behavior by manually maintaining records of aspects of their physical activity, including time points, durations, and/or other metrics (e.g., weight lifted, distance traveled, repetitions, sets, etc.) of their exercise behavior. Exercise tracking systems and software have been recently developed to provide some amount of assistance to a user interested in tracking his/her exercise behavior; however, such systems and methods still suffer from a number of drawbacks. In particular, many systems require a significant amount of effort from the user (e.g., systems rely upon user input prior to and/or after a period of physical activity), capture insufficient data (e.g., pedometers that estimate distance traveled, but provide little insight into an amount of physical exertion of the user), provide irrelevant information to a user, and are incapable of detecting body-responses to physical activity at a resolution sufficient to provide the user with a high degree of body awareness. Other limitations of conventional biometric monitoring devices include one or more of: involvement of single-use electrodes, involvement of electrodes that have limited reusability, involvement of a single electrode targeting a single body location, involvement of a professional for electrode placement, use of adhesives for electrode placement, electrode configurations that result in user discomfort (e.g., strap-based systems), use of electrode configurations that are unsuited to motion-intensive activities of the user, use of wired systems that constrain mobility, and other deficiencies.

Furthermore, integration of biometric tracking systems into garments worn by a user is particularly challenging. Challenges include: coupling conductors to garments in a manner that still allows the garment to move and stretch with motion of the user; preventing a conducting fluid (e.g., sweat) from shorting various conductors coupled to a garment; creating an assembly that can be washed and reused without compromising the circuitry and processors through which the system operates; routing signal conduction pathways across seams of a garment; accommodating a high connection density; customizing garment fit to a user; transmitting signals acquired by way of the garment to a processing system; having a system that has an expandable number of sensors that are easily interchangeable; mitigating noise resulting from friction between fabric layers and signal conduction pathways and other sources; and designing for aesthetics, scalability, and maintaining electrode-skin contact during use by a user.

There is thus a need in the biometric device field to create a new and useful garment integrated sensing system and method. This invention provides such a new and useful system and method.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. System

Figure 1:
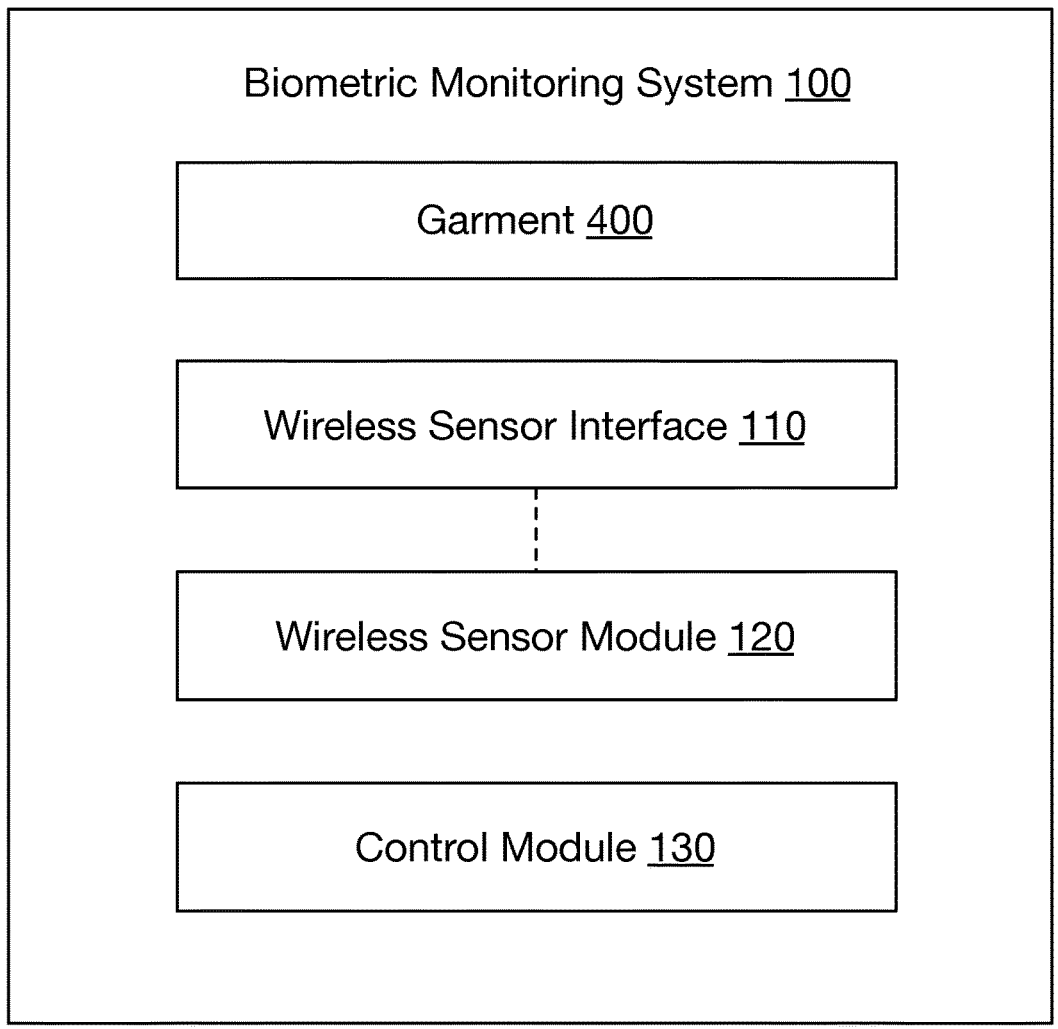
FIG. 1 depicts a schematic diagram of an embodiment of a system for monitoring biometric signals of a user.
Figure 2:
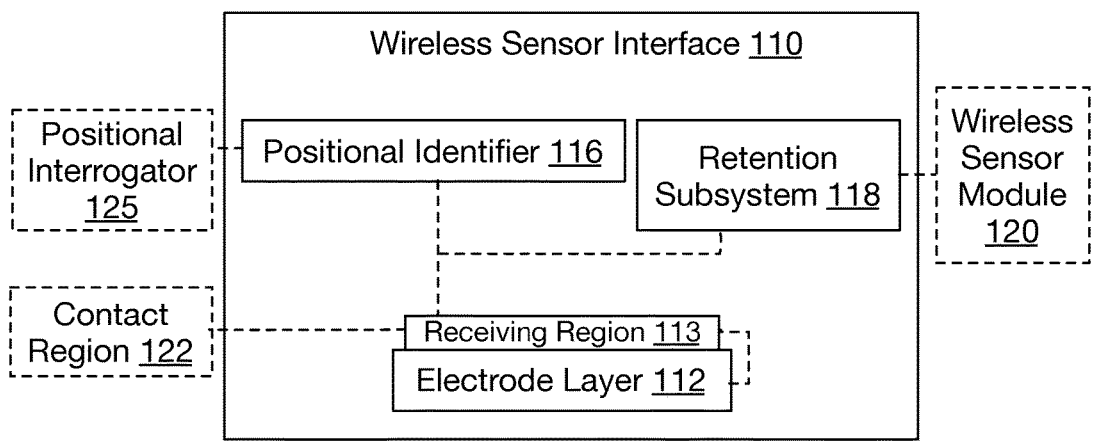
FIG. 2 depicts a schematic diagram of an embodiment of a sensor interface of a system for monitoring biometric signals of a user.
Figure 3:
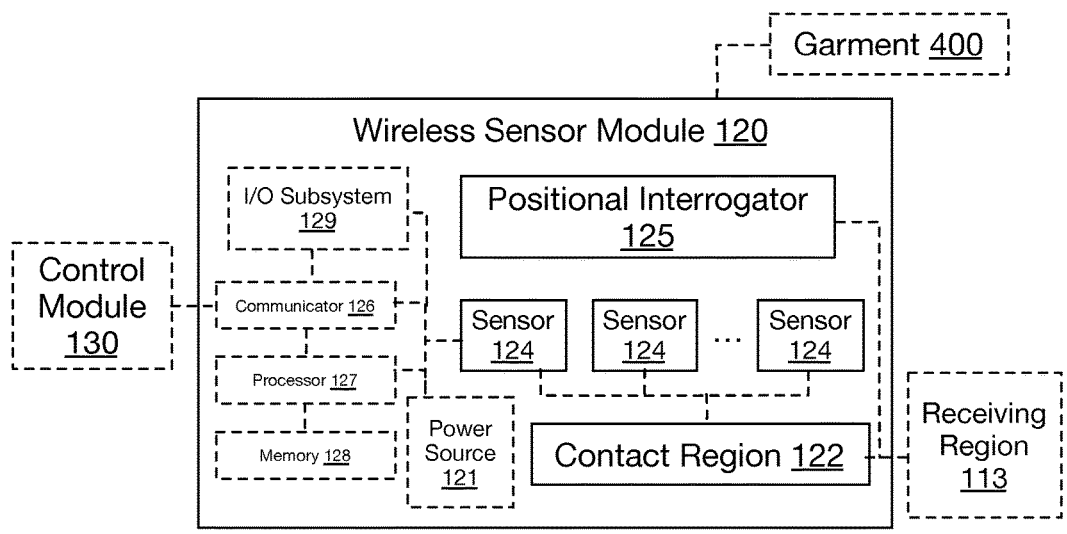
FIG. 3 depicts a schematic diagram of an embodiment of a sensor module of a system for monitoring biometric signals of a user.

As shown in FIGS. 1-3, an embodiment of a system 100 for garment-integrated biometric sensing includes: one or more wireless sensor interfaces 110 integrated with a garment 400, wherein a wireless sensor interface includes an electrode layer 112, a positional identifier 116, and a retention subsystem 118; one or more wireless sensor modules 120, removably coupled to a corresponding wireless sensor interface 110, wherein a wireless sensor module includes a contact region 122, one or more sensors 124, and a positional interrogator 125; and a control module 130 communicatively coupled to the one or more wireless sensor modules 120. As described in more detail below, one or more variations of the system 100 can omit one or more of the above elements, in providing a suitable garment-integrated biometric sensing system.

The system 100 functions to facilitate the collection of biometric signals from a user wearing the garment 400, wherein the biometric signals can be detected from a user who is performing some type of activity (e.g., physical activity, etc.) and subsequently processed to provide information to the user in substantially near real time, such that the user can gain insights into how to maintain or improve performance of the activity in a beneficial manner. The system 100 can additionally or alternatively function to provide a modular and adjustable set of available biometric signals for analysis, network a set of wireless sensor modules 120 together through the use of a control module 130, provide secure retention locations for coupling a set of wireless sensor modules 120 and/or a control module 130 to the garment 400 by way of the wireless sensor interface(s) 110, determine the available set of biometric signals based on the location(s) of the wireless sensor module(s) 120 with respect to the garment 400, and dynamically adjust the set of available biometric signals based on collected and/or recorded biometric signals from the set of wireless sensor modules 120. As such, the system 100 can be used to measure biometric signals (or other signals) of the user in a flexible, dynamic, automatic, and expandable manner, as well as with improved comfort and fit, improved appearance compared to conventional options, and with improved integration between the wireless sensor module(s) 120 and/or the control module 130 and the garment.

As such, the system 100 can be configured for one or more of the following: providing a universal garment-integrated biometric monitoring system that is compatible with various types of garments 400, where each type of garment 400 supports measurement of a subset of biometric signals detectable from the entire body of the user (e.g., it is difficult to measure signals originating from biceps or triceps muscles with a tank top garment); locating wireless sensor modules 120 close to the point of measurement of the biometric signal, while avoiding noise originating from movement of the conductive path in the garment between the measurement location and the control module 130; and providing single removable wireless sensor modules that can be purchased individually and/or in sets for different measurement applications, allowing the cost of the system 100 to scale according to the desired application of the user (e.g., an upper-body heart rate measurement kit containing a garment 400 and one wireless sensor module 120, a lower-body heart rate kit containing a garment 400 and two wireless sensor modules 120, etc.).

In variations, the system 100 is configured to facilitate transmission of detected bioelectrical signals generated at multiple body regions of a user who is exercising (e.g., performing aerobic exercise, performing anaerobic exercise), wherein a plurality of wireless sensor interfaces 110 of the system 100 can be positioned at multiple body regions of the user, in order to generate a holistic representation of one or more biometric parameters relevant to activity of the user. As used herein, a "biometric signal", "bioelectrical signal", or "biometric" means any value, measurement, or score related to a human body signal. A biometric signal, for instance, may include a value, measurement, data, or score associated with movement, heart rate, respiration, muscle activity, or other biometric measurement. For example, a biometric signal can refer specifically to a heart rate measurement (e.g., beats per minute) as determined by a processing device based on a bioelectric signal (e.g., biopotential electrocardiograph signal). Alternatively, a biometric signal can refer to a measurement of movement (e.g., distance traveled, acceleration, jerk, etc.), respiration measurement (e.g., breath per minute, length of breaths, regularity of breath), muscle activity (e.g., muscle exertion, muscle balance), or other value, measurement, or score associated with movement, heart rate, respiration, and/or muscle activity. Bioelectrical signals transmittable by the system 100 can additionally include one or more of: electromyography (EMG) signals, electrocardiography (ECG) signals, electroencephalograph (EEG) signals, galvanic skin response (GSR), bioelectrical impedance (BIA), and any other suitable bioelectrical signal of the user. The system 100 can, however, be configured to transmit any other suitable biosignal data of the user, including one or more of: motion data (e.g., velocity data, acceleration data, jerk data, vibration data, etc.), location data, skin temperature data, environmental data (e.g., ambient temperature data, light data, imaging data, etc.), and any other suitable data. Additionally or alternatively, the system 100 can be configured to transmit any other suitable type of signal, including one or more of: audio signals, communication signals, human produced signals, device produced signals, and any other type of signal that can be transferred through a conductive medium or wirelessly.

Preferably, the system 100 is configured to be integrated with a garment 400 worn by a user during a period of physical activity, as described in U.S. application Ser. No. 14/541,446, entitled "System and Method for Monitoring Biometric Signals" and filed on 14 Nov. 2014, U.S. application Ser. No. 14/079,629, entitled "Wearable Architecture and Methods for Performance Monitoring, Analysis, and Feedback" and filed on 13 Nov. 2013, U.S. application Ser. No. 14/079,621, entitled "Wearable Performance Monitoring, Analysis, and Feedback Systems and Methods" and filed on 30 Jan. 2014, U.S. application Ser. No. 14/699,730, entitled "Biometric Electrode System and Method of Manufacture" and filed on 29 Apr. 2015, and U.S. application Ser. No. 14/724,420, entitled "Biometric Signal Conduction System and Method of Manufacture" and filed on 17 Jun. 2015, each of which is incorporated herein in its entirety by this reference. As such, portions of the system 100 are preferably configured to provide a liquid-tight interface (e.g., by way of a seal) between conductive components of the garment 400 and conductive portions of the wireless sensor interface(s) 110, the wireless sensor module(s) 120, and/or the control module 130, upon coupling of the wireless sensor module(s) 120 to the wireless sensor interface(s) 110 and/or coupling of the control module 130 to the garment 400, such that sweat or water which may be intermingled with the fabric(s) of the garment cannot penetrate the system 100 and interfere with sensitive portions (e.g., conductive leads) of the system 100 during use. Even further, in relation to integration with a garment 400, the wireless sensor interface(s) 110 is/are preferably configured to be washable (i.e., hand-washable, machine washable, etc.), to be sweat-proof, to sustain stretching of the integrated fabric, to be scalable (e.g., in terms of size, in terms of volume of manufacture, etc.), to be low-maintenance, and to function properly and in a robust manner in relation to seams of the garment. Furthermore, the system 100 is preferably configured to be incorporated into a garment independent of the nature of the particular garment (e.g., underwear, outerwear, loose-fitting, tight-fitting, synthetic material, natural material, or any other characteristics particular to various suitable garments).

The system 100 is preferably configured to be used by a user who is away from a research or clinical setting, such that the user is interfacing with a portion of the system 100 while he or she undergoes periods of physical activity in a natural, non-clinical setting (e.g., at a gym, outdoors, etc.).

The system 100 can additionally or alternatively be configured to be operated by a user who is in a research setting, a clinical setting, or any other suitable setting for the collection of biometric data.

The system 100 is preferably configured such that communication between the wireless sensor modules 120 and the control module 130 is wireless, but in some variations, all or part of the communication between these and other elements of the system 100 can occur via wired communication. As such, in some variations of the system 100, the wireless sensor modules 120 may not be "wireless", and/or the wireless sensor interfaces 110 may not be "wireless".

1.1 System—Supporting Elements

Figure 9:
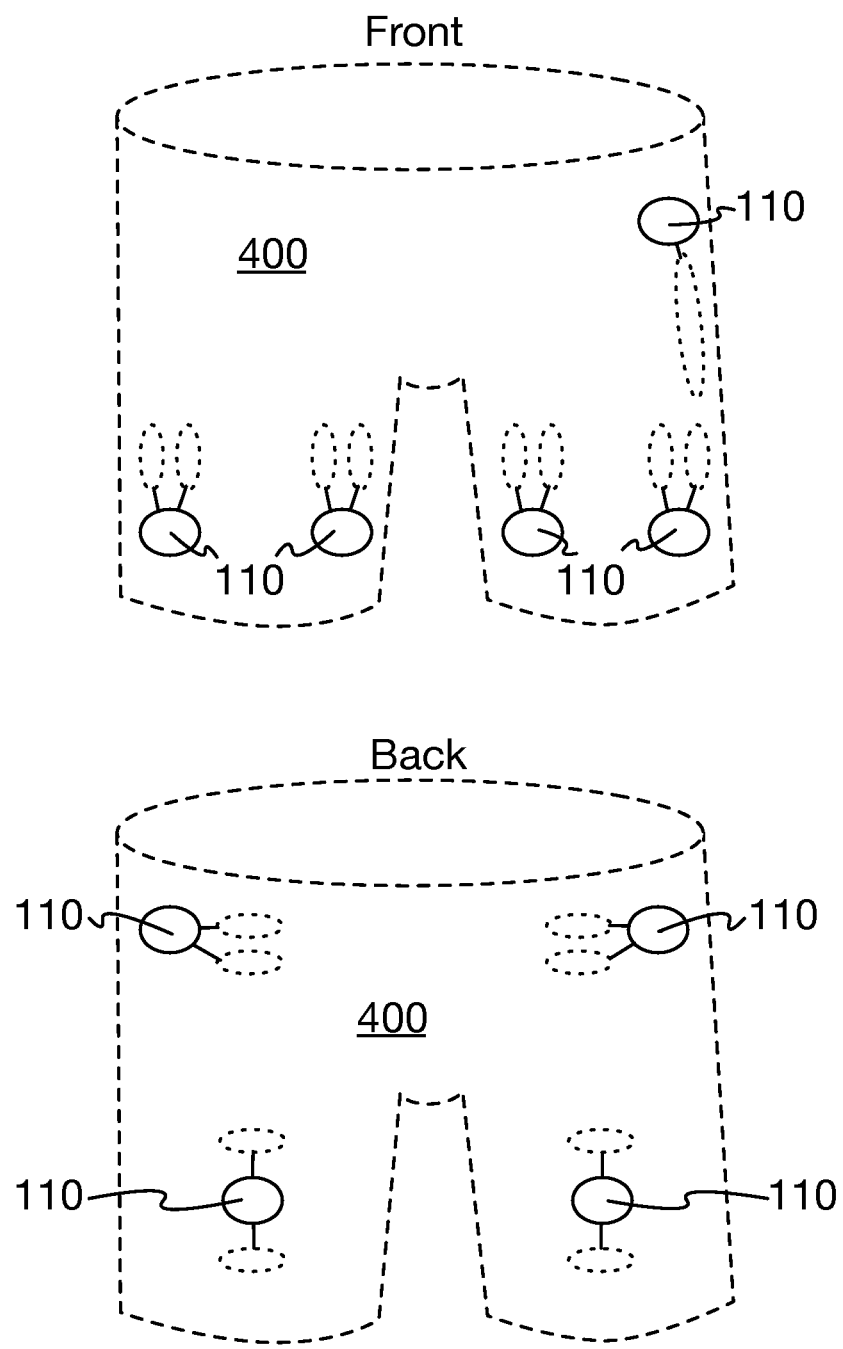
FIG. 9 depicts front and back views of an example embodiment of a system for monitoring biometric signals of a user.

As noted above and as shown in FIG. 9, the system 100 can be integrated with a wearable garment 400. Portions of the system 100 can be affixed to the garment 400 (e.g., using a set of screws, rivets, pins, adhesives, sewing, etc.); However, the system 100 can additionally or alternatively provide coupling between electronic components and/or to the garment 400 by way of one or more of: crimp connectors, snap connectors, stitching, a chemical bond, and any other suitable coupling agent.

The garment 400 is preferably composed of a form-fitting and washable material that is configured to be worn on at least a portion of a user's body. In one variation, portions of the system 100 can be coupled to the exterior of the garment 400, to an inner lining of the garment 400, be removably coupled with respect to any suitable portion of the garment 400, or traverse a portion of the garment. Coupling between portions of the system 100 and the garment 400 can be permanent (e.g., by way of heat binding, by way of gluing, by way of stitching, etc.) or non-permanent (e.g., by using Velcro™, by using fasteners, by using buttons, by using a light adhesive, etc.). The garment 400 can thus include a stretchable and/or compressive fabric comprising natural and/or synthetic fibers (e.g., nylon, lycra, polyester, spandex, etc.) to promote coupling (i.e., electrical coupling, mechanical coupling) and/or reduce motion artifacts that could otherwise result from relative motion between the skin of the user and the system 100.

In examples, the garment 400 can include any one or more of: a top (e.g., shirt, jacket, tank top, bra etc.), bottom (e.g., shorts, pants, capris etc.), elbow pad, knee pad, arm sleeve, leg sleeve, socks, undergarment, neck wrap, glove, and any other suitable wearable garment. Furthermore, the garment 400 can include one or more slots, pouches, ports, bases, pathways, channels, cradles, or other features by which wireless sensor interfaces 110, wireless sensor modules 120, and/or one or more control modules 130 can permanently or removably couple to the garment 400. The garment 400 can represent specialized clothing for a particular sport or activity, such as cycling attire, rock climbing clothing, and other activity specific clothing.

The system 100 described below can, however, cooperate with or otherwise be integrated with any other suitable elements as described in one or more of: U.S. application Ser. No. 14/541,446, entitled "System and Method for Monitoring Biometric Signals" and filed on 14 Nov. 2014, U.S. application Ser. No. 14/079,629, entitled "Wearable Architecture and Methods for Performance Monitoring, Analysis, and Feedback" and filed on 13 Nov. 2013, U.S. application Ser. No. 14/079,621, entitled "Wearable Performance Monitoring, Analysis, and Feedback Systems and Methods" and filed on 30 Jan. 2014, U.S. application Ser. No. 14/699,730, entitled "Biometric Electrode System and Method of Manufacture" and filed on 29 Apr. 2015, and U.S. application Ser. No. 14/724,420, entitled "Biometric Signal Conduction System and Method of Manufacture" and filed on 17 Jun. 2015. Additionally or alternatively, the system 100 can be configured to interface with any other suitable element(s).

1.2 System—Overview of Integrated Biometric Signal Interface

As noted above and as shown in FIGS. 1-3, an embodiment of the system 100 includes: a wireless sensor interface 110, including an electrode layer 112, a positional identifier 116, and a retention subsystem 118 a wireless sensor module 120, including a contact region 122, one or more sensors 124, and a positional interrogator 125; and a control module 130. Again, as described in more detail below, one or more variations of the system 100 can omit one or more of the above elements, in providing a suitable interface between a garment and a mating object. In particular, the system 100 can include a wearable garment 400 having one or more wireless sensor interfaces 110 to which removable wireless sensor modules 120 can physically and electrically couple. In addition, the wireless sensor interface 110 can include an electrode layer 112 that interfaces with a user's body. In one or more embodiments, the electrode layer 112 can transmit (e.g., conduct) a biometric signal from the user's body to a wireless sensor module 120. Upon receiving a biometric signal, the removable wireless sensor module 120 can wirelessly transmit data representative of the biometric signal to a wireless control module 120. The control module 130 can store, process, analyze and otherwise manipulate the data representative of the biometric signal to provide one or more metrics or biometric signals.

The system 100 can provide a variety of features that provide improved function, use, durability, and comfort when compared to conventional biometric detecting systems. For example, the system 100 can be incorporated within a garment 400 such that it provides the benefits of a biometric monitoring system, but does so within the comfort and familiarity of standard clothing that a user would wear regardless. For example, the system 100 can include one or more wireless sensor modules 120 and/or control modules 130 that may be implemented within a wearable garment 400 without requiring straps, adhesives, or other features that may cause discomfort when worn by a user. Moreover, the wireless sensor interfaces 110 can include one or more features to enhance the durability of the wearable garment, provide customizable and flexible wireless sensor module 120 placement, and additional comfort to a user. For example, the system can include one or more wireless sensor modules 120 and/or control modules 130 that are removable and/or easily replaceable, thus reducing wear and tear on a wearable garment 400 and the removable devices over time (e.g., when the garment is washed), as well as the expense of the garment 400.

In addition to providing an increase in comfort, the system 100 can include various features that provide for a user-friendly system (e.g., in terms of intuitiveness, in terms of ease of use, etc.). For example, each wireless sensor interface 110 can include a positional identifier 116 that is based on a position of a wireless sensor interface 110 within the garment 400. Upon a user coupling a wireless sensor module 120 to a wireless sensor interface 110, the wireless sensor module 120 can use the position identification to automatically identify, and inform a control module 130, which type(s) of signal (e.g., heart rate, muscle activity) the wireless sensor module 120 will be providing to the control module 130. Thus, the system 100 can provide an automatic setup process where a user simply has to couple a wireless sensor module 120 to a wireless sensor interface 110 to initiate the system 100 to start recording biometric signals in a manner that is specific to the configuration of the wireless sensor module(s) and/or to the activity type of the user.

Additionally, the system 100 can provide a configuration of wireless sensor modules 120 in communication with a control module 130 that enables the control module 130 to receive high fidelity biometric signals to determine various biometrics. In particular, the system 100 can include multiple wireless sensor modules 120 arranged using a variety of configurations to provide various types of biometrics. For example, removable wireless sensor modules 120 can have various configurations to measure different types of signals such as, for example, muscle activity, electromyography (EMG) signals, single-lead electrocardiogram (ECG) signals, skin temperature, resistance, change of breathing, etc., as will be described further below.

1.2.1 System—Wireless Sensor Interface

As shown in FIG. 2, the wireless sensor interface 110 preferably includes an electrode layer 112, a positional identifier 116, and a retention subsystem 118. The wireless sensor interface 110 functions to removably couple the wireless sensor module 120 to the garment 400 (or other element interfacing with the electrode layer 112), bring portions of the wireless sensor module 120 into electrical communication with one or more body regions of a user, and to permit the wireless sensor module 120 to ascertain the position of the wireless sensor module 120 in relation to the garment 400. Preferably, the wireless sensor interface 110 is integrated with the garment 400, by means of one or more manufacturing techniques described above, but alternatively the wireless sensor interface 110 can be removably and/or temporarily affixed to the garment 400 (e.g., with Velcro, as a removable insert in a portion of the garment 400, an adhesive, etc.). Preferably, the wireless sensor interface 110 does not impact the comfort of the garment 400 when the garment 400 is worn by the user, and is devoid of unsuitably abrasive or perturbing features adjacent to the user when the garment 400 is worn. Each wireless sensor interface 110 is preferably located strategically with respect to the garment 400, such as, for example, proximal major muscle group regions and/or heart regions of the user when the garment 400 is worn. Preferably, the wireless sensor interface 110 is configured such that the garment 400 can be washed and/or worn without adversely impacting the performance of the wireless sensor interface 110 with respect to other portions of the system 100, as well as without impacting the athletic performance of the user.

The wireless sensor interface 110 is preferably shaped such that a wireless sensor module 120 can be placed on (e.g., in, around, over, proximal, adjacent to, etc.) the wireless sensor interface 110 in retaining the wireless sensor module 120 upon removably coupling the wireless sensor module 120 to the wireless sensor interface 110. In particular, the wireless sensor interface 110 preferably includes one or more conductive silicone regions (e.g., impressions, recessed portions, protrusions, etc.) that mechanically retain a corresponding wireless sensor module 120 and electrically couple portions of the wireless sensor interface 110 and the wireless sensor module 120. Other portions of the wireless sensor interface 110 are preferably made substantially of flexible plastic, but alternatively all or part of the wireless sensor interface 110 can be made of various fabrics, hard plastics, conductive polymers, insulating polymers, metals, or any other suitable material. As a further alternative, the wireless sensor interface 110 can be composed of multiple fabric and/or non-fabric flexible layers, portions of which are sewn into the garment 400.

The wireless sensor interface 110 preferably includes an electrode layer 112, which functions to electrically couple portions of the wireless sensor interface 110 to a skin region of the user. The electrode layer 112 is preferably flexible, but can alternatively be rigid, semi-rigid, or composed of both flexible and inflexible regions. At least portions of the electrode layer 112 are preferably conductive so as to provide an electrical coupling interface to a skin or other body region of a user. For example, a portion of the electrode layer 112 can be composed of a conductive polymer. Regions of the electrode layer 112 disposed adjacent to the skin region of the user are preferably substantially flat, but alternatively can include raised and/or recessed portions to enhance electrical coupling to the skin region of the user and to enhance mechanical coupling to the body of the user to reduce motion of the electrode. In variations of the electrode layer 112, the electrode layer 112 can include a single flat layer, a discontinuous flat layer, both conductive and insulating regions, a tacky and/or sticky coating, a pliable region, a resilient region, raised bumps, or any other suitable configuration. The electrode layer 112 is preferably similar to the biometric electrode system described in U.S. application Ser. No. 14/699,730, entitled "Biometric Electrode System and Method of Manufacture" and filed on 29 Apr. 2015, which is herein incorporated in its entirety by reference. In an example embodiment of the electrode layer 112, the electrode layer 112 includes a signal communication region comprising a set of conductive leads, in which portions of the conductive leads are electrically coupled to the contact region 122 of the wireless sensor module 120, and also includes a set of biosensing contacts, made of a conductive polymer, positioned adjacent to a skin region of the user, the set of biosensing contacts coupled to the set of conductive leads. Alternatively, the electrode layer 112 can comprise any other suitable biometric electrode.

The electrode layer 112 preferably includes a receiving region 113, coupled to the electrode layer 112, and which functions to electrically and mechanically couple portions of the wireless sensor interface 110 to the wireless sensor module 120. Specifically, the receiving region 113 preferably mates to the contact region 122 of a corresponding wireless sensor module 120, thereby retaining the wireless sensor module 120 on the garment 400 in a removable manner and bringing portions of the wireless sensor module 120 into electrical contact with the electrode layer 112 that is, in turn, in electrical contact with the user. The receiving region 113 is preferably composed of a conductive polymer, but can alternatively comprise both conductive and insulating regions, as well as a combination of rigid and flexible regions, or any other suitable material configuration that provides electrical and mechanical coupling between the wireless sensor module 120 and the wireless sensor interface 110. The receiving region 113 is preferably at a side of the electrode layer 112 opposing the side of the electrode layer 112 that is adjacent to the skin region of the user. In variations, the receiving region 113 can include protrusions (e.g., raised bumps), mating male/female contacts and/or snaps, a substantially flat region with high coefficient of friction, a tacky region, multiple raised areas, and any other suitable configuration.

The wireless sensor interface 110 can include a positional identifier 116, which functions to identify the position of the wireless sensor interface 110 with respect to the garment 400 (and/or another suitable reference point). The positional identifier 116 is preferably a component with an intrinsic identifying characteristic, but alternatively can be a component with an encoded identifying characteristic or any other suitable identifier. For example, the positional identifier 116 can be a resistor with an intrinsic electrical resistance value that is known to correspond to a particular position of the wireless sensor interface 110 on the garment 400. Alternative examples of the positional identifier 116 include a resistor-capacitor and/or resistor-capacitor-inductor network with a known time response to an applied voltage and/or current, a passive backscatter radiofrequency identification (RFID) chip that provides encoded position identification when queried, or any suitable active and/or passive component with a known communicable and/or measurable signature that corresponds to the position and/or location of the wireless sensor interface 110 with respect to the garment 400.

Figure 5:
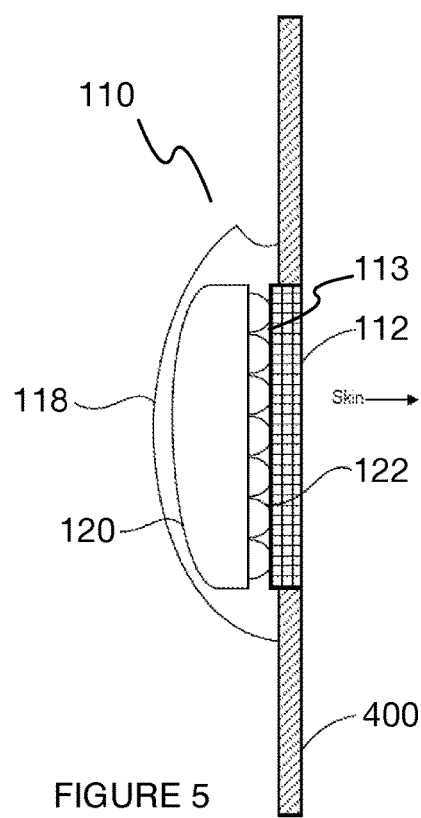
FIG. 5 depicts a specific example of a configuration of a system for monitoring biometric signals of a user.

The wireless sensor interface 110 preferably includes a retention subsystem 118, which functions to mechanically retain the wireless sensor module 120 upon coupling of the wireless sensor module 120 to the wireless sensor interface 110. The retention subsystem 118 can preferably withstand typical usage of an athletic garment 400 without failing or degrading performance of the wireless sensor module 120 and/or the wireless sensor interface 110. In particular, the retention subsystem 118 can preferably hold the contact region 122 of the wireless sensor module 120 in suitable electrical communication with the receiving region 113 of the electrode layer 112 of the wireless sensor interface 110. As shown in FIG. 5, the retention subsystem 118 can include a fabric layer configured to form a pocket around the electrode layer 112. Alternatively, the retention subsystem 118 can be configured in a similar manner to variations and examples of portions of the mount system as described in U.S. application Ser. No. 14/541,446, entitled "System and Method for Monitoring Biometric Signals", filed on 14 Nov. 2014, and U.S. application Ser. No. 14/869,398, entitled "Garment Integrated Electrical Interface System and Method of Manufacture", filed on 29 Sep. 2015, each of which is incorporated herein in its entirety by this reference. Further alternative embodiments of the retention subsystem 118 can include one or more straps, clips, snaps, male/female Velcro regions, magnets, buttons, or any suitable mechanism for retaining the wireless sensor module 120 proximal the wireless sensor interface 110.

1.2.2 System—Wireless Sensor Module

As shown in FIG. 3 the wireless sensor module 120 can include a contact region 122, one or more sensors 124, and a positional interrogator 125. The wireless sensor module 120 can additionally include one or more of: a communicator 126, a processor 127, a memory 128, and an input/output (I/O) subsystem 129. The wireless sensor module 120 functions to detect (measure, sense, record, etc.) one or more biometric signals of the user, as well as to query the position of the wireless sensor interface 110 by way of the positional identifier 116 of the wireless sensor interface 110. The wireless sensor module 120 can additionally function to communicate the position of the wireless sensor interface 110 and therefore, the position of the wireless sensor module 120, to the control module 130, as well as to perform selections and/or computations regarding the biometric signals being detected by way of the wireless sensor module. The wireless sensor module 120 is preferably rugged, lightweight, aesthetically pleasing, and self-contained in a unitary enclosure (e.g., watertight enclosure). The wireless sensor module 120 can be contained in a substantially ovoid enclosure, but can alternatively be enclosed in a rectangular prismatic casing or any other suitable three-dimensional volumetric enclosure. In some embodiments, the wireless sensor module 120 can have a greater number of sensors than signals that can be output simultaneously, requiring determination of which signals are to be collected (detected, measured, sensed, etc.) and/or output (transmitted, communicated, processed, stored, etc.). In particular, the wireless sensor module 120 can have a single output channel, or multiple output channels. In some embodiments, a number of wireless sensor module(s) 120 are interchangeable with one another and can couple to any wireless sensor interface 110. In alternative embodiments, a subset of types of wireless sensor modules 120 can be compatible with corresponding types of wireless sensor interface 110 but not with other types of wireless sensor interface 110, and this correspondence can be one-to-one or any other suitable categorical correspondence. In a first variation of the wireless sensor module 120 shown in FIG. 8A, the wireless sensor module 120 couples to the wireless sensor interface 110 via a male-female coupling interface, wherein the wireless sensor module 120 is the male entity and the wireless sensor interface 110 is the female entity. In a second variation, the wireless sensor module 120 couples to the wireless sensor interface 110 via a male-female coupling interface, but the wireless sensor module 120 is the female entity and the wireless sensor interface 110 is the male entity. In alternative variations, both the wireless sensor module 120 and the wireless sensor module 110 can include male and female portions of a male-female coupling interface between the wireless sensor module 120 and the wireless sensor interface 110.

Figure 10A:
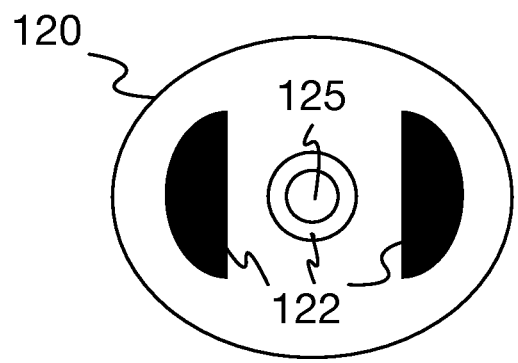
FIG. 10A depicts a specific example configuration of a sensor module of a system for monitoring biometric signals of a user.
Figure 10B:
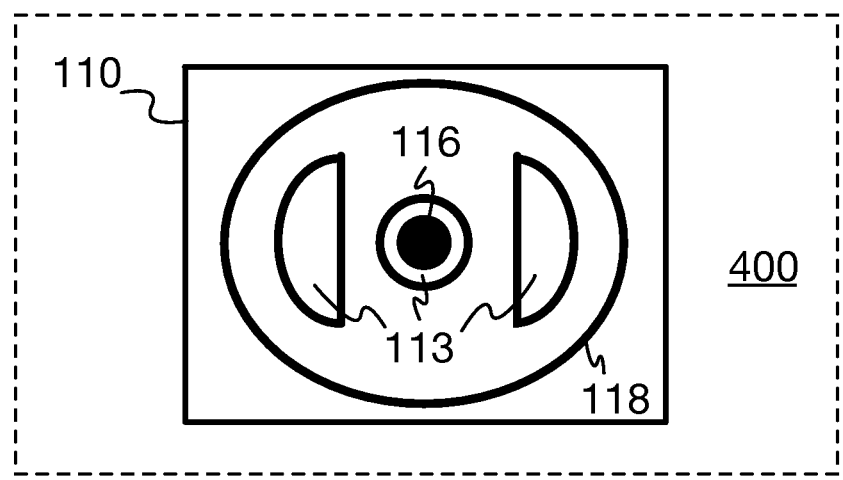
FIG. 10B depicts a specific example configuration of a sensor interface of a system for monitoring biometric signals of a user.

The wireless sensor module 120 preferably includes a contact region 122, which functions to bring the wireless sensor module 120 into electrical contact with the receiving region 113 of the electrode layer 112 of the wireless sensor interface 110. In some variations, one of which is shown in FIGS. 10A-10B, the contact region 122 also functions to bring the positional interrogator 125 of the wireless sensor module 120 into electrical communication with the positional identifier 116 of the wireless sensor interface 110. The contact region 122 preferably includes a set of contacts that interfaces with a set of receiving positions of the receiving region 113, but alternatively can be a substantially flat surface that mates to a corresponding flat surface of the receiving region 113, or any other suitable configuration that provides the requisite electrical communication between the contact region 122 and the receiving region 113.

In particular, the wireless sensor module 120 preferably makes a single-channel differential analog measurement by way of the contact region 122 interfaced with the receiving region 113. As such, the contact region 122 can include a differential pair of individual contacts, each contact in the pair capable of individually electrically connecting to a skin region of the user by way of the receiving region 113 of the electrode layer 112 or to an internal ground connection of the sensor. In this way, the wireless sensor module 120 can make single-ended (i.e., referenced to an internal ground connection) or differential analog measurements.

The wireless sensor module 120 preferably includes one or more sensors 124, which function to detect and/or record biometric signals of the user. The sensors 124 are preferably in electrical communication with the contact region 122 and preferably detect biometric signals by way of electrical contact with a body region of the user, but alternatively can detect biometric signals that require no such contact. For example, one of the sensors 124 can detect an electromyography signal by detecting a change in the electrical properties of a skin region of the user by way of electrical contact, and additionally or alternatively one of the sensors 124 can detect a level of athletic activity of a user by detecting motion data without the need for electrical contact with the skin region of the user. Various types of sensors 124 can include: magnetoencephalography sensors, galvanic skin response sensors, electrooculography sensors, electromyelography sensors, electromyography sensors, bioelectrical impedance sensors, electrocardiography sensors, electroencephalography sensors, respiratory rate sensors, acceleration sensors, velocity sensors, jerk sensors, vibration sensors, motion sensors, temperature sensors, light sensors, imaging sensors, gyroscopic sensors, microelectromechanical systems (MEMS) sensors, and any other suitable type of sensor of biometric or biometrically-correlated signals. In a further example illustrated by FIG. 9, the biometric signal can be from a reference electrode, measuring the biopotential from the body of a user related to ambient electronic noise from the user. The ambient noise measurement can be combined with other biometric signal measurements to improve signal-to-noise ratio, signal fidelity, or any other suitable aspects of the biometric signal measurements.

The wireless sensor module 120 preferably includes a positional interrogator 125, which functions to interface with and query the positional identifier 116 to identify the position of the wireless sensor interface 110 with respect to the garment 400. In some embodiments, the positional interrogator 125 can include a current or voltage source that applies a voltage to or passes a current through the positional identifier 116 to measure the known or intrinsic characteristic of the positional identifier 116, which can be, for example, the characteristic resistance of a resistor of the positional identifier 116. In this example, the intrinsic characteristic that is measured is correlated with a position on the garment 400, enabling the positional interrogator 125 to identify the position of the wireless sensor interface 110 (e.g., a resistance of ~1,000 Ohms corresponds to a wireless sensor interface 110 positioned on a chest region of the garment 400, and a resistance of ~10,000 Ohms corresponds to a wireless sensor interface 110 positioned on a sleeve region of the garment 400). In other embodiments, the positional interrogator 125 is an RFID transceiver that queries an RFID chip of the positional identifier 116 and receives an encoded signal containing the position of the wireless sensor interface 110 on the garment 400. In an alternative variation, the positional interrogator 125 includes a logic circuit that presents a set of contacts at the contact region 122, and the receiving region 113 presents a set of receiving contacts that short-circuits portions of the logic circuit upon coupling of the contact region 122 and the receiving region 113, such that a logic output of the logic circuit is produced which corresponds to the position of the wireless sensor interface 110 on the garment 400. Alternatively, the positional interrogator 125 can be any suitable component or set of components that interfaces with the positional identifier 116 in order to detect the position of the wireless sensor interface 110 on the garment 400. As a further alternative, the positional interrogator 125 can store a unique identifier, and transmit the unique identifier upon interfacing with the positional identifier 116. The unique identifier can be an identifier of the position of the wireless sensor module 120, the position of the wireless sensor interface 110, the type of wireless sensor module 120, or any other suitable identifier. In some embodiments, the wireless sensor module 120 can self-configure which biometric signal type(s) to detect, transmit, and/or process based on the positional information detected (collected, measured, recorded, etc.) from the positional interrogator 125/positional identifier 116 interface.

The wireless sensor module 120 can also include a communicator 126, which functions to wirelessly transmit and/or receive signals between the wireless sensor module 120 and the control module 130. These signals can include one or more of: the biometric signals sensed by the sensor(s) 124 of the wireless sensor module 120, signals provided by the electrode layer 112, additional signals (e.g., signals containing data regarding the position of the wireless sensor interface 110, signals containing metadata regarding other transmitted/received signals, etc.), and any other suitable signal(s). In particular, the communicator 126 can broadcast the position-based configuration of the wireless sensor module 120 and the nature of the biometric signal being measured to the control module 130. The communicator 126 is preferably a short-range wireless communication radio (e.g., a Bluetooth transceiver), but can alternatively be an intermediate or long range wireless communication transceiver, an optical data transceiver (e.g., an LED/photodiode pair), an auditory data link (e.g., a speaker/microphone pair), or any other suitable wireless communication mechanism. In some embodiments, the communicator 126 can transmit compressed data related to the measured biometric signal(s) with the frequency content of the measured biometric signal(s).

The wireless sensor module 120 can also include a processor 127, which functions to perform computational operations on the sensed biometric signal(s), as well as other signals detected by the wireless sensor module 120. Other signals can include signals containing data regarding the position of the wireless sensor interface 110, instructions from the control module 130, or any other related signals. Examples of computational operations performed by the processor 127 include: transforming, scaling, shifting, integrating, differentiating, convolving, deconvolving, filtering, combining, dividing, adding, and subtracting one or more sensed biometric signals and/or other signals as described. The processor 127 can additionally or alternatively function to automatically locate the wireless sensor module 120 with respect to the garment 400 by way of the interface between the positional identifier 116 and the positional interrogator 125, and/or to automatically select one or more biometric signal outputs to automatically transmit to the control module 130.

The wireless sensor module 120 can also include a memory 128, which functions to record and store biometric signals and other signals on the wireless sensor module 120. The signals can be recorded on the memory 128 before, after, or substantially simultaneously with transmission of the signals to the control module 130 by way of the communicator 126.

The wireless sensor module 120 can also include an I/O subsystem 129, which functions to allow the user to provide input directly to and receive output directly from the wireless sensor module 120. This can occur with or without intermediation by the control module 130. Examples of input portions of the I/O subsystem 129 include: buttons, switches, microphones, touch sensors (e.g., capacitive touch sensors), proximity sensors (e.g., infrared motion sensors), or any other suitable input mechanism. Examples of output portions of the I/O subsystem 120 include: lights/LEDs, speakers (e.g., to emit an audible tone or sequence of tones), a display (e.g., an LCD, LED display, a scrolling text display, etc.), or any other suitable output mechanism.

The wireless sensor module 120 can also include a power source 121, which functions to provide power to the wireless sensor module 120. The power source 121 is preferably a battery (e.g., a coin cell, a lithium-polymer battery, or similar), but can additionally or alternatively harvest energy from the ambient environment (e.g., a solar cell, thermoelectric generator, etc.) or the user (e.g., a kinetic energy storage device, body temperature differential thermoelectric generator, etc.).

1.2.3 System—Control Module

Figure 4:
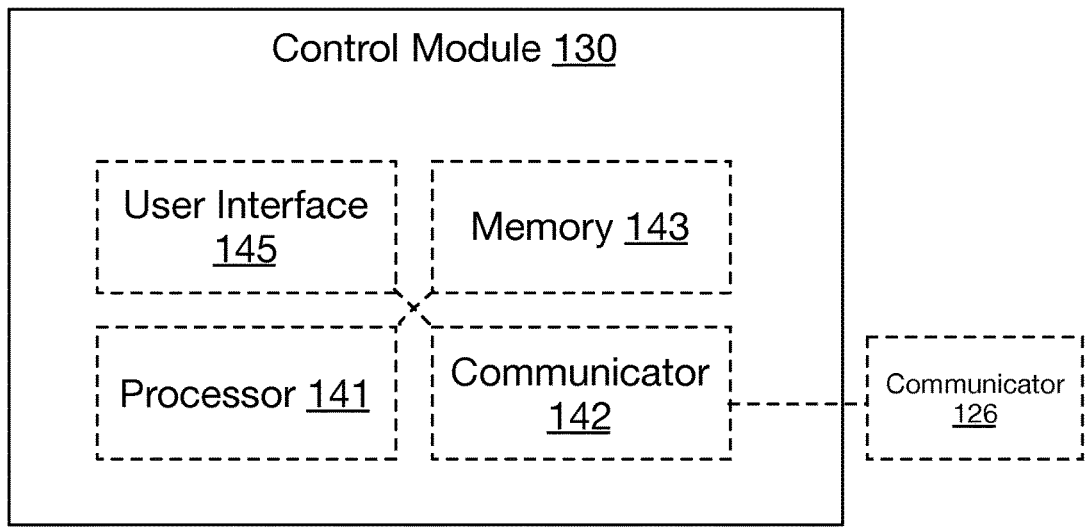
FIG. 4 depicts a schematic diagram of an embodiment of a control module of a system for monitoring biometric signals of a user.
Figure 6:
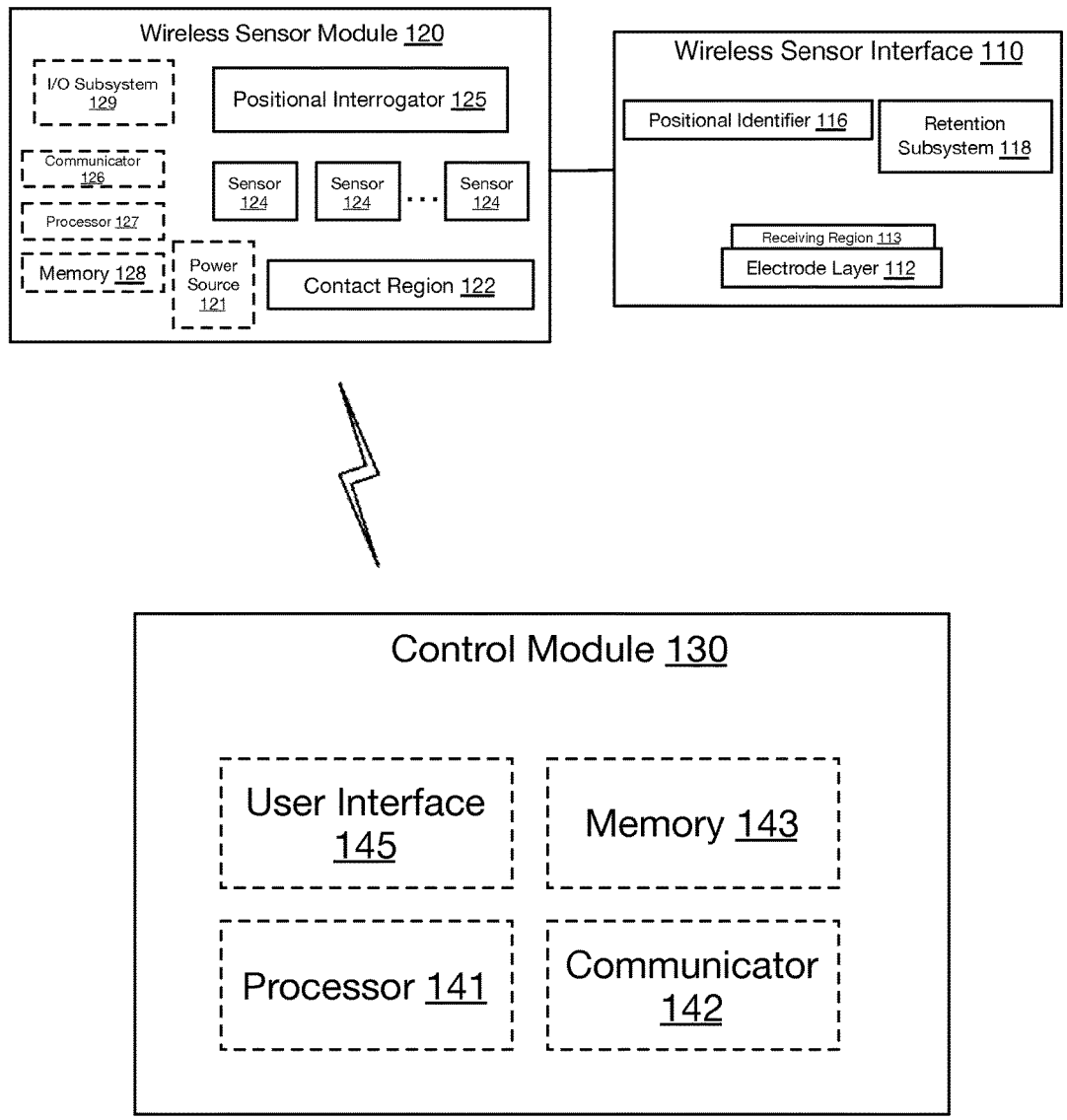
FIG. 6 depicts an embodiment of a system for monitoring biometric signals of a user, indicating communication pathways.
Figure 7:
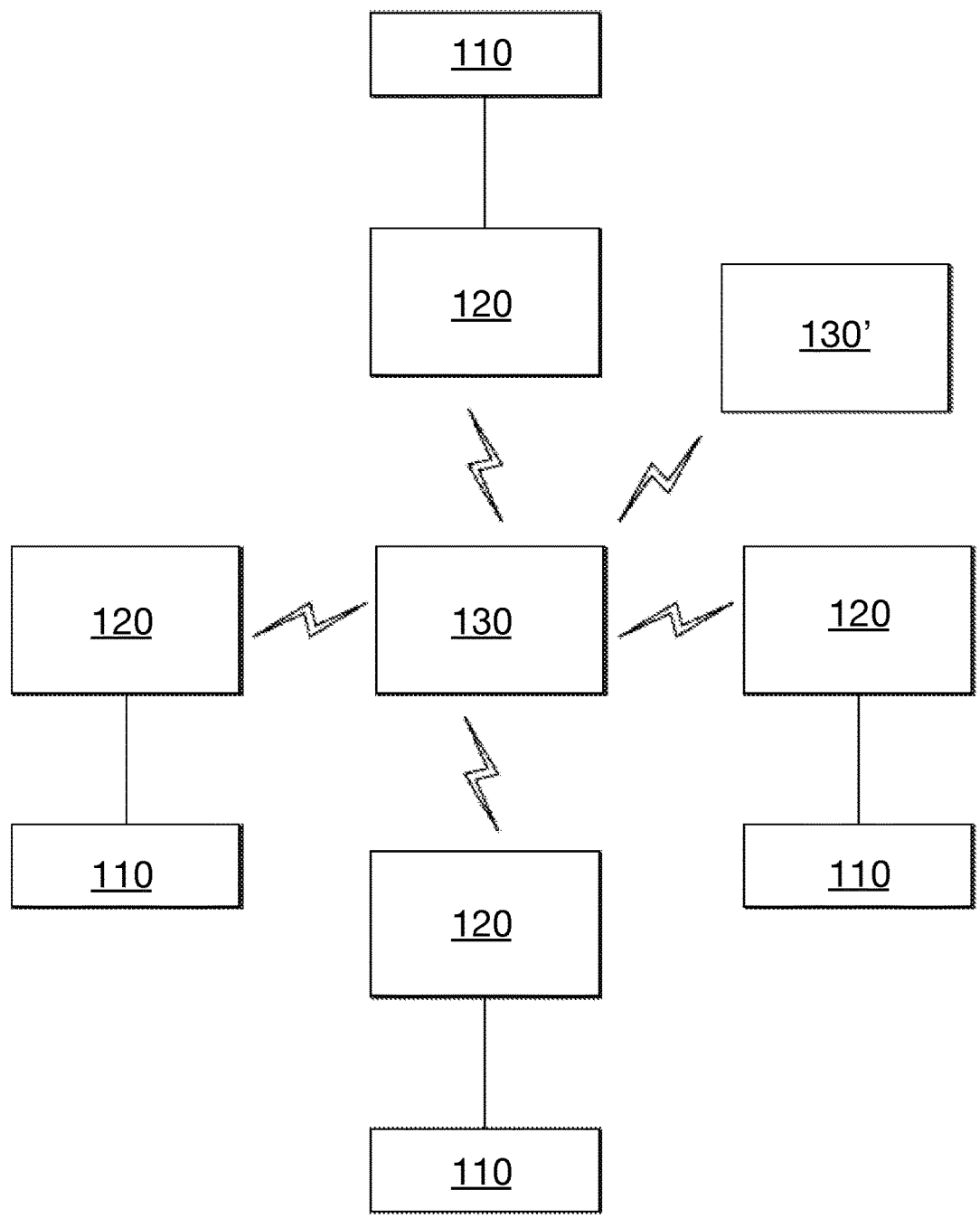
FIG. 7 depicts an embodiment of a system for monitoring biometric signals of a user, comprising a plurality of sensor modules, sensor interfaces, and control modules.

As shown in FIGS. 4,6, and 7, the system 100 includes a control module 130, which functions to receive biometric signals transmitted from the wireless sensor module(s) 120. The control module 130 can also function to query certain biometric signals or sets of biometric signals from a wireless sensor module 120 based on the position of the wireless sensor module 120 and the corresponding wireless sensor interface 110. The control module 130 can also function as an interface between a user and the one or more wireless sensor modules 120, allowing the user to control the operation of the system 100. For example, the user can indicate by way of the control module 130 that they prefer the one or more sensors to collect and transmit electromyography signals, and the control module 130 can mediate the collection of such signals based on such a preference. Preferably, the control module 130 is a mobile and/or portable device. Alternatively, the control module 130 can be a substantially stationary device (e.g., a server, a desktop computer, a distributed network of servers and/or desktop computers, etc.). In some embodiments, the control module 130 is coupleable to the garment 400. In alternative embodiments, the control module 130 is separate from the garment 400 (e.g., as a wrist-mounted wearable device, as a head-mounted wearable device, as a mobile computing device, etc.). In still further embodiments, the system 100 can include a control module 130 and a control module 130', which cooperatively function to control and interface with portions of the system 100, as shown in FIG. 7.

The control module 130 can include a processor 141, which functions to perform computational operations on the biometric signals and other signals received from the wireless sensor module(s) 120, as well as additional computational tasks. Such additional computational tasks can include, for example, coordinating the one or more wireless sensor modules 120 with respect to which biometric signals each of the wireless sensor modules 120 is tasked to detect. However, functions of the processor 141 can additionally or alternatively be implemented in any other suitable processing module interfacing with or incorporated into the system 100. The control module 130 can also include a communicator 142, which functions to communicate with wireless sensor module(s) 120. Preferably, this communication occurs by way of a communicator 126 of the wireless sensor module 120. The control module 130 can also include a memory 143, which functions to store biometric signal data, wireless sensor interface 110 position data, user preference data, user instruction data, and other related data. The control module 130 can also include a user interface 145, which functions to allow a user to provide inputs and receive outputs directly from the control module 130. The user interface 145 can include an input device (e.g., buttons, switches, microphones, touch sensors, physical or virtual keyboard, etc.) as well as an output device (e.g., display, small screen, LED indicators, scrolling text display, speakers, etc.) for facilitating communication with the user.

The control module 130 can include embodiments, variations, and examples of the control module described in U.S. application Ser. No. 14/541,446, entitled "System and Method for Monitoring Biometric Signals" and filed on 14 Nov. 2014; however, the control module 130 can additionally or alternatively include any other suitable control module 130.

1.2.4 System—Specific Examples

Figure 8A:
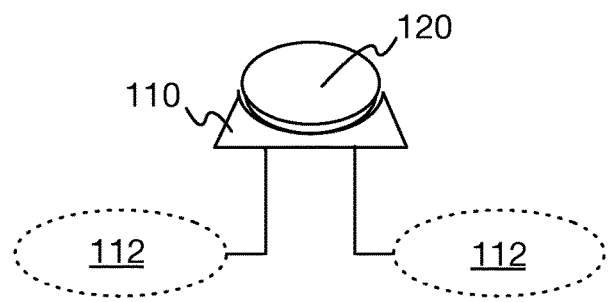
FIGS. 8A-8C depict different example configurations of contacts and electrode layers in embodiments of a system for monitoring biometric signals of a user.
Figure 8B:
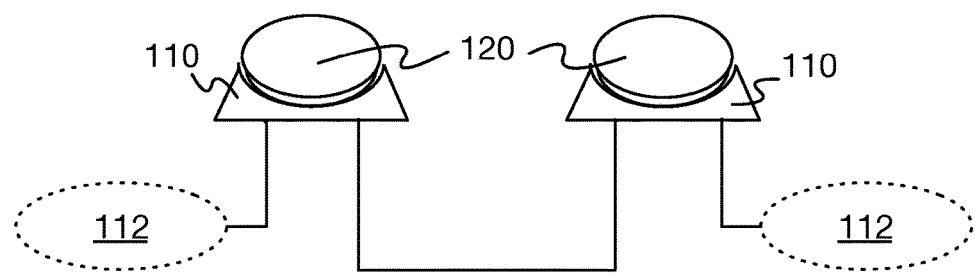
Figure 8C:
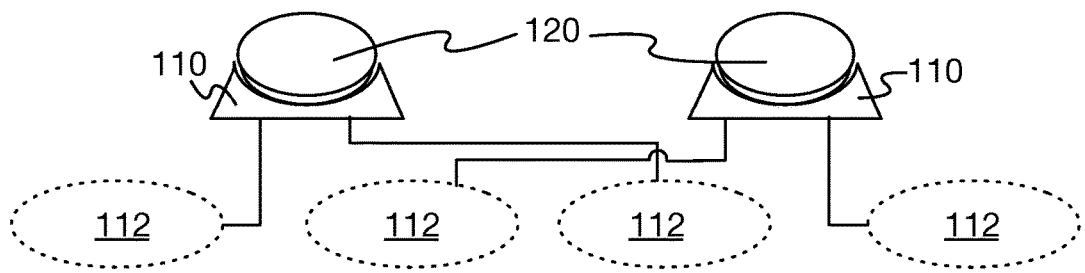

In a first example of the system 100, two wireless sensor modules 120 are coupled to a short-sleeved compression shirt (i.e., a garment 400) by way of two corresponding wireless sensor interfaces 110. The first of the two wireless sensor modules 120 is coupled to the garment at the first wireless interface 110 in a superior-left torso region of the garment, and the second of the two wireless sensor modules 120 is coupled to the garment at the second wireless interface 110 at an inferior-left torso region of the garment. The wireless sensor interfaces 110 are mounts substantially as described in U.S. application Ser. No. 14/869,398, entitled "Garment Integrated Electrical Interface System and Method of Manufacture", filed on 29 Sep. 2015, and in U.S. application Ser. No. 14/702,129, entitled "System and Method for Monitoring Biometric Signals", filed 1 May 2015. A control module 130 substantially of the form described in U.S. application Ser. No. 14/541,446, entitled "System and Method for Monitoring Biometric Signals", filed on 14 Nov. 2014, is coupled to a pair of compression shorts that are not physically linked to the short-sleeved compression shirt, but the control module is in wireless communication with each of the two wireless sensor modules 120. In a first mode of operation, the first wireless sensor module 120 of the first specific example automatically begins collecting and transmitting a two-point heart rate measurement to the control module 130 upon coupling to the first wireless sensor interface 110, based on detection of its position at the superior-left torso region of the garment by way of measurement of an internal resistance of the positional identifier 116 of the first wireless sensor interface 110. In the first mode of operation, the second wireless sensor module 120 automatically begins collecting and transmitting respiratory rate data to the control module 130, based on detection of its position at the inferior-left torso region of the garment by way of measurement of an internal resistance of the positional identifier 116 of the second wireless sensor interface 110. In a second mode of operation, the first and second wireless sensor modules 120 are placed by the user at a third wireless interface 110 and a fourth wireless sensor interface 110, respectively, and upon detection and transmission of the respective positions are designated to collect and transmit separate single-ended analog heart rate measurements, referenced to an internal ground connection of each wireless sensor module, in producing a combined two-point ECG signal at the control module 130. In a third mode of operation, automatically selected by the control module 130 based on the signals collected in the second mode of operation, the first and second wireless sensor modules 120 are designated to collect and transmit differential analog heart rate measurements, in producing a combined, two channel, four point ECG signal at the control module 130. Depictions of the various single and multiple wireless sensor module configurations of this example embodiment are shown in FIGS. 8A-C.

In a second example embodiment of the system 100, a spandex unisuit (i.e., a garment 400) includes a wireless sensor interface 110 proximal each of the major muscle groups (e.g., the upper and lower arm regions of both sleeves, the upper and lower leg regions of both pantlegs, the chest region, the abdominal region, the upper and lower back regions, etc.). Each wireless sensor interface 110 has a retention subsystem 118 in the form of an elastic fabric pocket. Each of a set of interchangeable wireless sensor modules 120 can be placed in a corresponding pocket on the garment and thereby be brought into electrical contact with a corresponding skin region of a user proximal the closest muscle group as described above. An integrated circuit, located in the vicinity of each wireless sensor interface 110, stores a unique address corresponding to the position of the wireless sensor interface 110 on the garment. Each wireless sensor module 120 includes a circuit that, upon interfacing with the integrated circuit of the wireless sensor interface 110, ascertains and communicates the position of the wireless sensor module 120 on the garment and, therefore, the muscle group to which it is most proximal. In a first mode of operation, each wireless sensor module 120 detects, processes, and stores an electromyography signal related to the muscle activity of the muscle group to which it is most proximal and tags the stored EMG signal with the positional information. In a second mode of operation, the wireless sensor modules 120 are removed from the wireless sensor interfaces 110 of the garment and wirelessly synced with a smartphone (i.e., the control module 130), at which time the biometric signals tagged with the positional information are combined and processed at the control module 130 to produce an overall time history of the muscle activity of the user organized by muscle group (e.g., the muscle group corresponding to the positional information).

The system 100 can include any other suitable elements configured to enhance electrical and mechanical coupling of a wireless sensor module 120 or control module 130 to a garment 400, to easily and removably couple/decouple the wireless sensor module 120 or control module 130 to/from the wireless sensor interface 110 or other garment interface, to dissipate static, to shield the conductors from noise, to prevent moisture damage to elements of the system 100, and/or to facilitate manufacturing of the system 100. Furthermore, as a person skilled in the art will recognize from the previous detailed description and from the figures, modifications and changes can be made to the system 100 without departing from the scope of the system 100.

2. Method of Biometric Signal Sensing

Figure 11:
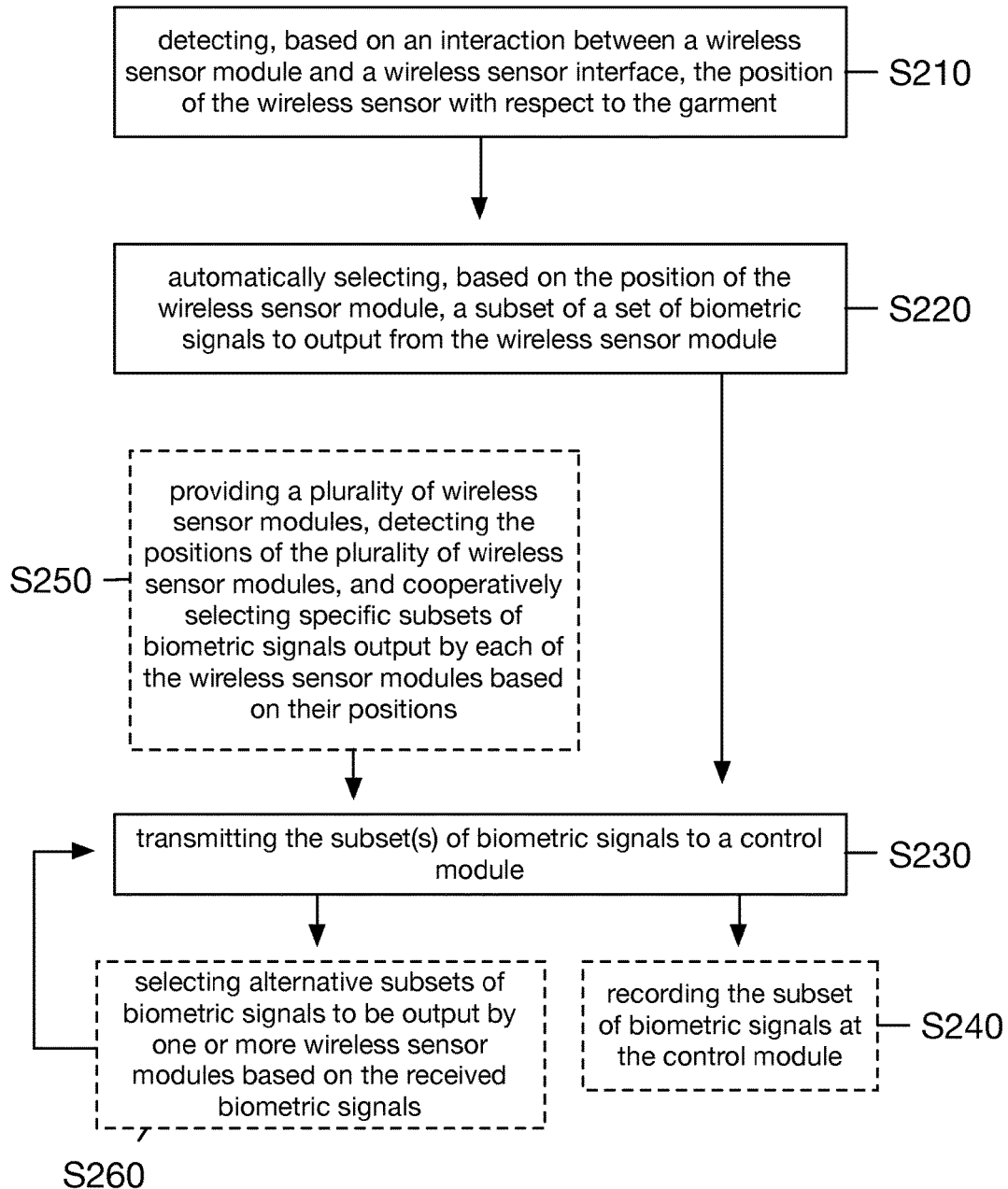
FIG. 11 depicts an embodiment of a method for monitoring biometric signals of a user.

As shown in FIG. 11, an embodiment of a method 200 for monitoring biometric signals of a user comprises: detecting, based on an interaction between the wireless sensor module and a wireless sensor interface of a garment, a position of the wireless sensor module with respect to the garment S210; automatically selecting, based on the position of the wireless sensor module, a subset of a set of biometric signals to output from the wireless sensor module S220; and transmitting the subset of biometric signals to a control module S230. The method 200 can additionally or alternatively include: recording the subset of biometric signal(s) at the control module S240; providing a plurality of wireless sensor modules, detecting the positions of the plurality of wireless sensor modules and cooperatively selecting specific subsets of biometric signals output by each of the wireless sensor modules based on their positions S250; and selecting alternative biometric signals to be output by one or more wireless sensor modules based on the received biometric signals S260.

The method 200 functions to dynamically and automatically modify and utilize a network of garment-coupled biometric sensors and to record biometric signals from a user wearing the garment during the performance of an action or activity. The method 200 can additionally function to enhance the resource utilization of a biometric monitoring system with a limited number of input and output channels, by prioritizing specific biometric signals obtained from certain sensor positions over others. The method 200 is preferably performed by a system such as the system 100 described above, but alternatively it can be performed by any suitable system. The method 200 is preferably performed in conjunction with a garment such as the garment 400 used in conjunction with the system 100, but can alternatively be used in conjunction with any suitable garment for biometric signal sensing.

2.1 Method—Sensor Position Detection

Block S210 recites: detecting, based on an interaction between a wireless sensor module and a wireless sensor interface, the position of the wireless sensor module with respect to the garment. Block S210 functions to make data corresponding to the position of the wireless sensor module available to the wireless sensor module and/or the control module, which can in turn incorporate that data into other elements of the method 200. In Block S210, the interaction is preferably an interaction as described above between a positional interrogator 125 of a wireless sensor module 120 and a positional identifier 116 of a wireless sensor interface 110, but can alternatively be any suitable interaction between any suitable wireless sensor module and any suitable wireless sensor interface that results in identifying (detecting) the position of the wireless sensor module with respect to the garment. Variations of Block S210 can additionally or alternatively include sensing the position, generating position data based on the interaction, recording the position data, storing the position data, and/or transmitting the position data. In Block S210, an example of an interaction on which the detection is based is the measurement of the impedance of a portion of the wireless sensor interface by the wireless sensor module, and the correlation of the measured impedance with a set of known position-impedance pairs. A second example is the querying of a passive backscatter RFID chip of the wireless sensor interface by a RFID transceiver of the wireless sensor module, and the decoding of the received signal to obtain the position. Block S210 is preferably performed by the wireless sensor module, but can alternatively be performed by the control module, cooperatively by the wireless sensor module and the control module, cooperatively by the wireless sensor module, wireless sensor interface, and the control module, or by any suitable combination of elements of the system and/or auxiliary components.

2.2 Method—Selecting Biometric Signal Output

Block S220 recites: automatically selecting, based on the position of the wireless sensor module, a subset of biometric signals from a set of biometric signals that can be output by the wireless sensor module. Block S220 functions to intelligently adjust the type and/or number of biometric signal outputs provided by the wireless sensor module, based on its position on the garment. In an example, Block S220 can include automatically selecting a subset of biometric signals including a heart rate measurement, wherein the full set of biometric signals can include a heart rate measurement, an electromyography measurement, an accelerometer measurement, and a galvanic skin response measurement. The full set of biometric signals can alternatively or additionally include any suitable biometric measurement(s). In particular, Block S220 can additionally or alternatively include determining the type of processing to be applied to a subset of biometric signals, by the control module or any other suitable processor. In Block S220, the subset of biometric signals can alternatively include multiple biometric signals from the full set, e.g., a heart rate measurement and an accelerometer measurement. Furthermore, one or more of the set of biometric signal types (e.g., accelerometer signal) can always be provided by the corresponding wireless sensor module/queried by the control module. Preferably, Block S220 is performed by the control module based on the detection of the position of a plurality of wireless sensor modules. Alternatively, Block S220 can be performed by the control module based on the detection of a single wireless sensor module, by the wireless sensor module itself, or cooperatively by one or more wireless sensor modules and the control module.

2.3 Method—Transmitting Selected Biometric Signals

The method 200 includes Block S230, transmitting the selected subset of biometric signals to the control module. Block S230 functions to send the sensed and/or recorded biometric signal(s) to the control module for further processing, analysis, and/or storage. Block S230 preferably includes wirelessly transmitting selected subsets of biometric signals over a short-range wireless communication protocol (e.g., Bluetooth), but can alternatively include transmitting signals over an intermediate or long range wireless communication protocol (e.g., WiFi, wireless Ethernet, etc.), transmitting via removable storage media (e.g., a USB data storage device is used to transfer the data between the wireless sensor module and the control module), transmitting over a wired and/or wireless network, or any other suitable action for transmitting, transferring, and/or receiving data. Block S230 is preferably performed by the wireless sensor module, but can alternatively be performed by an auxiliary transceiver coupled to the wireless sensor module, the control module, or any other suitable component.

2.4 Method—Recording of Selected Biometric Signals

As shown in FIG. 11, the method 200 can additionally or alternatively include Block S240, which recites: recording the selected subset of biometric signals at the wireless sensor module and/or the control module. Block S240 functions to store the sensed biometric signals instead of immediately processing and/or displaying them, though in some embodiments the sensed biometric signals can be stored and processed/displayed substantially simultaneously. In variations of the method 200 including processing of the sensor data, Block S240 can comprise storing of biometric signal data either at the wireless sensor module or at the control module for subsequent offloading or transmission to a processor (e.g., via removable digital storage media, a wired data link to a computing device, a data link to the control module, etc.).

2.5 Method—Selecting Cooperatively

The method 200 can additionally or alternatively include Block S250, which recites: providing a set of wireless sensor modules, detecting the corresponding position of each of the set of wireless sensor modules, and selecting the subset of biometric signals output by each of the set of wireless sensor modules based cooperatively on the positions of each of the set of wireless sensor modules. Block S250 functions to dynamically and automatically control the biometric signal outputs of a set (network) of wireless sensor modules by incorporating automatically-obtained knowledge of the positions of each of the set of wireless sensor modules into the determination of which biometric signal outputs should be output by each wireless sensor module. Detecting the corresponding position of each of the set of wireless sensor modules is preferably performed by each of the set of wireless sensor modules in cooperation with the control module, but can alternatively be performed by each of the set of wireless sensor modules in isolation, the control module in isolation, an auxiliary detector separate from either the wireless sensor module or the control module, or any other suitable detector. Selecting the subset of biometric signals output by each of the set of wireless sensor modules is preferably performed by the control module, but can alternatively be performed by each of the set of wireless sensor modules or any other suitable selector. In some embodiments, the control module can have a limited number of input channels, and selecting in Block S250 is functions to optimize or otherwise improve the quantity and quality of unique and/or useful biometric signals recorded at the control module given the limited number of input channels. In other embodiments, the wireless sensor modules can have a limited number of output channels, and selecting in Block S250 can function to optimize or otherwise improve the quantity and quality of unique and/or useful biometric signals recorded at the control module given the limited number of wireless sensor module output channels.

2.6 Method—Selecting Alternative Biometric Signals

The method 200 can additionally or alternatively include Block S260, which recites: selecting alternative subsets of biometric signals to be output by one or more wireless sensor modules based on previously received subsets of biometric signals. Block S260 functions to dynamically alter the selection of subsets of biometric signals output by the one or more wireless sensor modules, in response to aspects of the original selection of subsets of biometric signals. In some embodiments, selecting alternative subsets of biometric signals in Block S260 can be based on aspects of the original selection of subsets of biometric signals including the signal quality, (e.g., a wireless sensor module originally designated to provide heart rate data may be alternatively selected to provide accelerometer data because the heart rate data is determined to be of low quality). In other embodiments, selecting alternative subsets of biometric signals can be based on user preferences, e.g., a wireless sensor module originally designated to output galvanic skin response data may be alternatively selected to output electromyography data based on user preferences, which are input by the user via a user interface of the control module and/or the wireless sensor module. Alternatively, selecting alternative subsets of biometric signals based on previously received subsets of biometric signals can include selecting alternative subsets based on any suitable aspects of the previously received subsets of biometric signals.

2.7 Method—Specific Examples

In a first example of the method 200, a tablet computer is wirelessly linked to an ensemble of wireless sensor modules, coupled to a full-body garment at a set of wireless sensor interfaces positioned at distinct locations throughout the garment. Upon coupling of each wireless sensor module to a corresponding wireless sensor interface, the wireless sensor module automatically detects its position and begins collecting and transmitting EMG data tagged with its relative position on the garment to the tablet computer, as well as combined accelerometer and gyroscopic data likewise tagged with the position of the wireless sensor module. The position detection is performed by the mating of circuitry of each wireless sensor module with circuitry of the corresponding wireless sensor interface, producing a digital output containing an encoded position of the wireless sensor interface with respect to the garment. On the tablet computer, a three-dimensional representation of a human (i.e., the user) is rendered on the screen, complete with metrics of the muscle exertion measured at each of the ensemble of wireless sensor modules, correlated to their respective positions on the user. The rendering of the user is updated in near real-time to reflect the motion of the limbs of the user, computed from the ensemble of accelerometer and gyroscopic data collected from the ensemble of wireless sensor modules. This three-dimensional representation of the movement and muscle activity of the user can be used to compare the performance of the user to past performance of the user, idealized performance of the user or another user, or any other suitable basis of comparison. In particular, data pertaining to the position of the user's body in combination with the EMG data can allow an understanding of how muscle exertion intensity and temporal sequencing relates to the form of the user, given the movement and/or position of the user during performance of an activity.

In a second example of the method 200, a control module, coupled to a lower-body garment, is wirelessly linked to a wireless sensor module, coupled to the lower-body garment at one of a set of wireless sensor interfaces positioned at distinct locations throughout the lower-body garment. Upon coupling of the wireless sensor module to one of the set of wireless sensor interface, the wireless sensor module automatically detects its position and broadcasts its position to the control module. Detecting the position is performed by measuring the intrinsic resistance of a portion of the wireless sensor interface, producing a value that corresponds to a particular position of the wireless sensor interface with respect to the garment. The control module selects, based on the received position information indicating that the wireless sensor module is positioned at a gluteal region of the user, a subset of biometric signals including muscle activity signals, and instructs the wireless sensor module to measure and provide muscle activity signals. In at least one variation, the wireless sensor module detects and transmits muscle activity signals to the control module, which records the muscle activity data and may perform specific filtering and/or processing operations given that the biometric signal is an EMG signal and is measured from the gluteal region of the user. Upon decoupling the wireless sensor module from the first wireless sensor interface and coupling the wireless sensor module to a second wireless sensor interface of an upper-body garment worn by the user, the wireless sensor module broadcasts its new position to the control module. Detecting the new position is performed by signaling an RFID tag of the second wireless sensor interface with an RFID reader of the wireless sensor module. The control module selects, based on the received position information indicating that the wireless sensor module is positioned at an abdominal region of the user, a subset of biometric signals including motion data, and instructs the wireless sensor module to measure and provide signals including motion data. The wireless sensor module detects and transmits signals including motion data to the control module, which records the signals, including motion data. This specific example of the method 200 illustrates a dynamic and flexible method of monitoring biometric signals of a user via a modular and interchangeable wireless sensor module in communication with various wireless sensor interfaces and a control module.

Variations of the system 100 and method 200 include any combination or permutation of the described components and processes. Furthermore, various processes of the preferred method can be embodied and/or implemented at least in part as a machine configured to receive a computer-readable medium storing computer-readable instructions. The instructions are preferably executed by computer-executable components preferably integrated with a system and one or more portions of the control module 155 and/or a processor. The computer-readable medium can be stored in the cloud and/or on any suitable computer readable media such as RAMs, ROMs, flash memory, EEPROMs, optical devices (CD or DVD), hard drives, floppy drives, or any suitable device. The computer-executable component is preferably a general or application specific processor, but any suitable dedicated hardware device or hardware/firmware combination device, and additionally or alternatively, entity performing manual labor, can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams can represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

What is claimed is:

1. A biometric monitoring system, comprising:
a set of wireless sensor modules, each wireless sensor module coupled to a garment at a position on the garment and comprising a set of sensors configured to detect a set of biometric signal types at the position; and
a control module communicatively coupled to the set of wireless sensor modules and configured to select, for each wireless sensor module, a subset of the set of biometric signal types detected by the wireless sensor module, the subset of biometric signal types selected based on a detected position of the wireless sensor module.

2. The biometric monitoring system of claim 1, further comprising a set of wireless sensor interfaces, each of the wireless sensor interfaces located at a position in the garment and comprising a retention subsystem capable of mechanically coupling one of the wireless sensors to the garment at the position of the wireless sensor interface.

3. The biometric monitoring system of claim 1, wherein the set of sensors comprises one or more of: a first sensor configured to detect a heart rate measurement, a second sensor configured to detect an electromyography measurement, a third sensor configured to detect an accelerometer measurement, and a fourth sensor configured to detect a galvanic skin response measurement.

4. The biometric monitoring system of claim 1, wherein the set of wireless sensor modules comprises:
a first wireless sensor module at a position on the garment corresponding to a heart region, the selected subset of biometric signal types for the first wireless sensor comprising a heart rate measurement; and
a second wireless sensor module at a position on a garment corresponding to a muscle region of the user, the selected subset of biometric signal types of the second wireless sensor module comprising an electromyography signal.

5. A biometric monitoring system, comprising:
a set of wireless sensor modules, each wireless sensor module coupled to a garment at a position on the garment and comprising a set of sensors configured to detect a set of biometric signal types at the position;
wherein each wireless sensor module is communicatively coupled to a control module, the control module configured to select, for each wireless sensor module, a subset of the set of biometric signal types detected by the wireless sensor module, the subset of the biometric signal types selected based on a detected position of the wireless sensor module.

6. The biometric monitoring system of claim 5, wherein the control module comprises a stationary computing device remote to the garment.

7. The biometric monitoring system of claim 5, wherein the control module comprises a device mechanically coupled to the garment.

8. The biometric monitoring system of claim 5, wherein the control module comprises a mobile device separate from the garment.

9. The biometric monitoring system of claim 5, further comprising a set of wireless sensor interfaces, each of the wireless sensor interfaces located at a position in the garment and comprising a retention subsystem capable of mechanically coupling one of the wireless sensor modules to the garment at the position of the wireless sensor interface.

10. The biometric monitoring system of claim 5, wherein the set of sensors comprises one or more of: a first sensor configured to detect a heart rate measurement, a second sensor configured to detect an electromyography measurement, a third sensor configured to detect an accelerometer measurement, and a fourth sensor configured to detect a galvanic skin response measurement.

11. The biometric monitoring system of claim 5, wherein the set of wireless sensor modules comprises:
a first wireless sensor module at a position on the garment corresponding to a heart region, the selected subset of biometric signal types for the first wireless sensor comprising a heart rate measurement; and
a second wireless sensor module at a position on a garment corresponding to a muscle region of the user, the selected subset of biometric signal types of the second wireless sensor module comprising an electromyography signal.

12. A method, comprising:
receiving a detected position of a wireless sensor module, the detected position representing a position of the wireless sensor module on a garment, the wireless sensor module comprising a set of sensors configured to detect a set of biometric signal types at the position; and
selecting a subset of the set of biometric signal types detected by the wireless sensor module, the subset of the biometric signal types selected based on the detected position of the wireless sensor module.

13. The method of claim 12, wherein the detected position of the wireless sensor module is received by a control module from the wireless sensor module, and wherein the control module selects the subset of the set of biometric signal types.

14. The method of claim 13, wherein the control module comprises a stationary computing device remote to the garment.

15. The method of claim 13, wherein the control module comprises a device mechanically coupled to the garment.

16. The method of claim 13, wherein the control module comprises a mobile device separate from the garment.

17. The method of claim 12, wherein wireless sensor module selects the subset of the set of biometric signal types.

18. The method of claim 12, wherein each of the wireless sensor modules is mechanically coupled to a retention subsystem of a wireless sensor interface located at the detected position on the garment, and wherein the position of the wireless sensor module is detected based on an interaction between a positional interrogator of the wireless sensor module and a positional identifier of the wireless sensor interface.

19. The method of claim 12, wherein the set of sensors comprises one or more of:
a first sensor configured to detect a heart rate measurement, a second sensor configured to detect an electromyography measurement, a third sensor configured to detect an accelerometer measurement, and a fourth sensor configured to detect a galvanic skin response measurement.

20. The method of claim 12, wherein the set of wireless sensor modules comprises:
a first wireless sensor module at a position on the garment corresponding to a heart region, the selected subset of biometric signal types for the first wireless sensor comprising a heart rate measurement; and
a second wireless sensor module at a position on a garment corresponding to a muscle region of the user, the selected subset of biometric signal types of the second wireless sensor module comprising an electromyography signal.

\* \* \* \* \*